United States Patent
Panagiotopoulos et al.

(10) Patent No.: US 12,274,789 B2
(45) Date of Patent: Apr. 15, 2025

(54) ORAL COMPOSITIONS COMPRISING METHYLPREDNISOLONE SODIUM SUCCINATE

(71) Applicant: LABOMED PHARMACEUTICAL COMPANY S.A., Attica (GR)

(72) Inventors: Tsampikos Dimitrios Panagiotopoulos, Marousi (GR); Soultana Tziala, Artemida (GR)

(73) Assignee: LABOMED PHARMACEUTICAL COMPANY S.A., Koropi (GR)

( * ) Notice: Subject to any disclaimer, the term of this patent is extended or adjusted under 35 U.S.C. 154(b) by 399 days.

(21) Appl. No.: 17/251,784

(22) PCT Filed: Jun. 18, 2019

(86) PCT No.: PCT/EP2019/066022
§ 371 (c)(1),
(2) Date: Dec. 12, 2020

(87) PCT Pub. No.: WO2019/243337
PCT Pub. Date: Dec. 26, 2019

(65) Prior Publication Data
US 2021/0161822 A1  Jun. 3, 2021

(30) Foreign Application Priority Data
Jun. 18, 2018 (GR) .............................. 20180100264

(51) Int. Cl.
*A61K 9/19* (2006.01)
*A61K 31/573* (2006.01)
*A61K 47/10* (2017.01)
*A61K 47/26* (2006.01)

(52) U.S. Cl.
CPC .............. *A61K 9/19* (2013.01); *A61K 31/573* (2013.01); *A61K 47/10* (2013.01); *A61K 47/26* (2013.01)

(58) Field of Classification Search
CPC ........ A61K 9/19; A61K 31/573; A61K 47/10; A61K 47/26; A61K 9/143; A61K 9/0095

IPC ........... A61K 9/19,31/573, 47/10, 47/26, 9/143, 9/0095
See application file for complete search history.

(56) References Cited

U.S. PATENT DOCUMENTS

| | | | |
|---|---|---|---|
| 4,587,236 A | 5/1986 | Annen et al. | |
| 2007/0196415 A1* | 8/2007 | Chen | A61K 9/145 424/422 |

FOREIGN PATENT DOCUMENTS

| | | | |
|---|---|---|---|
| CN | 1850089 A | * | 4/2006 |
| CN | 102302460 A | * | 8/2011 |
| CN | 102293755 A | | 12/2011 |
| CN | 102743392 A | | 10/2012 |
| CN | 103371979 A | | 10/2013 |
| CN | 104434820 | * | 3/2015 |
| CN | 104434820 A | * | 3/2015 |
| TR | 201613662 A1 | * | 4/2018 |
| WO | WO-2011/101734 A2 | | 8/2011 |

OTHER PUBLICATIONS

Hayball, P.J., et al., "High dose oral methylprednisolone in patients with rheumatoid arthritis: pharmacokinetics and clinical response", Eur. J. Clin. Pharmacol, 42(1): p. 85-82 (1992).
Bin Saif, G.A., "Oral mega pulse methylprednisolone in alopecia universalis", Saudi Med. J., 2006. 27(5): p. 717-20.
Bin Saif, G.A., et al., "Efficacy and safety of oral mega pulse methylprednisolone for severe therapy resistant Alopecia areata", Saudi Med. J., 2012. 33(3): p. 284-91.
International Search Report and Written Opinion of the International Searching Authority, issued in PCT/EP2019/066022, mailed Nov. 5, 2019; ISA/EP.

* cited by examiner

*Primary Examiner* — Bethany P Barham
*Assistant Examiner* — Janet Joseph
(74) *Attorney, Agent, or Firm* — Harness, Dickey & Pierce, P.L.C.

(57) ABSTRACT

Stable, non-caking, pharmaceutical composition in the form of powder for oral solution comprising methylprednisolone sodium succinate and methods of making such compositions. The compositions comprise lyophilized methylprednisolone sodium succinate mixed with one or more water-soluble pharmaceutically acceptable excipients.

5 Claims, No Drawings

ORAL COMPOSITIONS COMPRISING METHYLPREDNISOLONE SODIUM SUCCINATE

FIELD OF THE INVENTION

The present invention relates to a pharmaceutical composition in the form of powder for oral solution, which comprises methylprednisolone sodium succinate, and a process for making the same.

BACKGROUND OF THE INVENTION

Methyprednisolone was first disclosed in U.S. Pat. No. 4,587,236. Methylprednisolone in the form of methylprednisolone sodium succinate is a potent synthetic corticosteroid. Its anti-inflammatory potency is greater than prednisolone in the ratio of 5 to 4. It has only minimal mineralocorticoid properties and has less tendency than prednisolone to induce sodium and water retention. It influences carbohydrate, protein, fat and purine metabolism, electrolyte and water balance, and the functional capacities of the cardiovascular system, the kidney, the skeletal muscle, nervous system and other organs and tissues. It exerts a suppressive effect on the immune response. Methylprednisolone sodium succinate may be used in conditions in which a rapid, intense glucocorticoid effect is required.

The chemical name for methylprednisolone sodium succinate is pregna-1,4-diene-3,20dione,21-(3-carboxy-1-oxopropoxy)-11,17-dihydroxy-6-methyl-monosodium salt, (6α,11β). The structural formula of methylprednisolone sodium succinate is represented below.

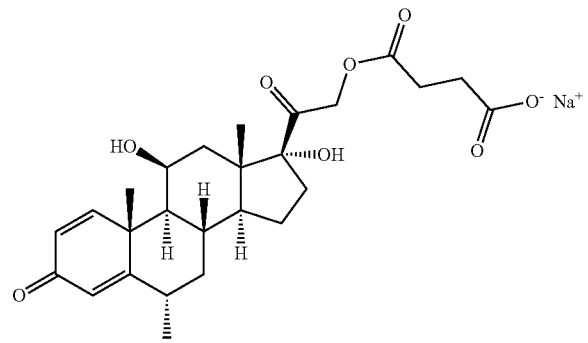

Methyprednisolone sodium succinate, occurs as a white, or nearly white, odorless hygroscopic, amorphous solid. Methylprednisolone and its derivatives according to, for example, CN102293755 are very unstable substances, especially in the presence of moisture.

Currently, methylprednisolone sodium succinate is only formulated as a sterile powder filled in vials for parenteral use. The powder filled in vials is produced by lyophilization (freeze-drying) and must be dissolved in water for injection before it can be injected.

An example of commercially available powder for injection is "Solu-Medrone™ 40, 125, 500, 1000, 2000 mg powder for solution for injection/infusion" which is marketed by Pfizer in several European countries. Each vial contains 40 mg, 125 mg, 500 mg or 1000 mg methylprednisolone (as methylprednisolone sodium succinate). This product also contains as excipients sodium hydroxide, sodium dihydrogen phosphate dihydrate and disodium hydrogen phosphate anhydrous. The 40 mg presentation also contains lactose.

Lyophilized Solu-Medrone™ powder is prepared by a process, which comprises suspension of methylprednisolone 21-hemisucinate in phosphate buffer solution, conversion to the sodium salt by slow addition of sodium hydroxide or sodium bicarbonate until essentially all solids are dissolved, addition of lactose, if present, and finally lyophilization of the resulting solution.

CN200810076703.8 discloses that, especially when formulating low dose methylprednisolone sodium succinate solutions, the active ingredient is easily hydrolyzed and addition of lactose as a stabilizer to inhibit hydrolysis is deemed necessary.

CN103371979 discloses a lyophilized methylprednisolone sodium succinate powder for solution for injection, which is prepared by dissolving the ingredients in a solvent, and then lyophilization, characterized in that the solvent is water for injection containing ethanol, and the ingredients in the formula are dissolved in the solvent. The resulting liquid contains 5-10% by volume of ethanol.

CN1850089 discloses a process for preparing methylprednisolone sodium succinate lyophilized powder for solution for injection as follows: methylprednisolone succinate, alkaline excipients, pH buffer solution and stabilizing agents, such as low molecular weight dextran, mannitol, lactose, glucose, maltose and other saccharides, poloxamers, chlorides and cyclodextrins, are mixed and dissolved in water for injections. After filtration, they are packaged in vials and lyophilized.

Furthermore, methylprednisolone sodium succinate is a very bitter substance with otherwise unpleasant taste. This is the main reason that it has been administered orally only in limited cases. For example, Hayball et. al. [Hayball, P. J., et al., "High dose oral methylprednisolone in patients with rheumatoid arthritis: pharmacokinetics and clinical response", Eur. J. Clin. Pharmacol, 1992. 42 (1): p. 85-82] administered a commercially available 1000 mg powder for injection of methylprednisolone sodium succinate both parenterally and orally on separate occasions, to eight elderly patients with active rheumatoid arthritis. In another case, Micromedex® database mentions that the commercially available powder for injection formulations of methylprednisolone sodium succinate can be administered orally after dissolving them in 200 milliliters of orange juice. The same method of administration has been used in the past in scientific research [Bin Saif, G. A., "Oral mega pulse methylprednisolone in alopecia universalis", Saudi Med. J., 2006. 27 (5): p. 717-20. & Bin Saif, G. A., et. al., "Efficacy and safety of oral mega pulse methylprednisolone for severe therapy resistant Alopecia areata", Saudi Med. J., 2012. 33 (3): p. 284-91].

As methylprednisolone sodium succinate is very unpalatable, a solution prepared from the currently marketed injection products i.e. a reconstituted solution from the methylprednisolone sodium succinate powder for solution for injection, has the drawback of a lingering bitter aftertaste and thus, poor patient compliance.

Thus, as a means of ensuring advanced patient compliance, the development of a pharmaceutical composition in the form of powder for oral solution comprising methylprednisolone sodium succinate with advanced organoleptic characteristics of the reconstituted solution is definitely an existing need.

WO2011/101734 discloses dry taste-masked powder for suspension compositions comprising methylprednisolone or its salts/derivatives. According to said document enhanced taste-masking capability of compositions is achieved by granulating, coating, complexing with water insoluble ion-exchange resin, forming inclusion complex of the active ingredient with cyclodextrin or forming solid-dispersions before admixing the active ingredient with other water insoluble additives or excipients.

It is also challenging to formulate powders for palatable methylprednisolone sodium succinate solutions instead of suspensions even when water-soluble taste masking agents are used. In these cases, the prior art indicates that high concentrations of taste masking agents are necessary for masking the bad taste of methylprednisolone sodium succinate. But such high quantities are proved to cause a negative effect on solubility, resulting in the formation of suspensions or colloids, with the presence of visible particles that become apparent upon reconstitution.

Additionally, there are many processing difficulties in preparing methylprednisolone sodium succinate powder compositions, since methylprednisolone sodium succinate is known to be hygroscopic, have poor flow, and tendency to form cakes, which adversely affect its manufacture into solid dosage forms when using conventional techniques such as dry mixing. CN1850089, for example, indicates that when methylprednisolone sodium succinate prepared by aseptic packaging, the active ingredient absorbs moisture easily. In this case, the production environment should be strictly controlled, and the production cost becomes high. Such poor manufacturing characteristics, which adversely affect uniformity of the dosage form, may also affect the drug's dissolution and its bio-availability.

The present invention addresses the problems of the prior art knowledge by advantageously providing a pharmaceutical composition in the form of powder for oral solution comprising methylprednisolone sodium succinate with advanced characteristics such as flowability, uniformity and physicochemical stability. The present invention also provides an oral solution, after dissolving the powder typically with water, with advanced organoleptic characteristics.

SUMMARY OF INVENTION

The present invention provides pharmaceutical compositions in the form of powder for oral solution comprising methylprednisolone sodium succinate and methods of making such compositions.

Advantageously the present invention provides a stable, non-caking pharmaceutical composition in the form of powder for oral solution comprising methylprednisolone sodium succinate. Furthermore, the present invention provides an oral pharmaceutical solution, after dissolving the powder typically with water, which exhibits exceptional taste and aftertaste.

The pharmaceutical composition in the form of powder for oral solution according to the present invention comprises a mixture of lyophilized methylprednisolone sodium succinate and one or more water-soluble pharmaceutically acceptable excipients.

Preferably, the pharmaceutical composition in the form of powder for oral solution according to the invention comprises a mixture of lyophilized methylprednisolone sodium succinate and one or more water-soluble pharmaceutically acceptable excipients, selected from the group consisting of a diluent (filler), a sweetener, a lubricant, a flavouring agent, a buffering and/or alkalizing agent, an antimicrobial agent, an antioxidant, a binder, a glidant, and a colourant.

In a preferred embodiment, the pharmaceutical composition in the form of powder for oral solution according to the invention comprises a mixture of lyophilized methylprednisolone sodium succinate and a diluent, which is mannitol, lactose or sorbitol, a sweetener, which is sucralose or sodium saccharin and a lubricant, which is sodium benzoate.

In another aspect, the present invention provides an efficient, cost-effective and robust method for making a stable, non-caking, pharmaceutical methylprednisolone sodium succinate composition in the form of powder for oral solution.

DETAILED DESCRIPTION OF THE INVENTION

The present invention provides a pharmaceutical composition in the form of powder for oral solution comprising methylprednisolone sodium succinate and methods of making such compositions.

The term "lyophilized methylprednisolone sodium succinate" means methylprednisolone sodium succinate in lyophilized form, which does not contain any pharmaceutical excipients except for, possibly, buffering and/or alkalizing agents.

The term "buffered lyophilized methylprednisolone sodium succinate" means methylprednisolone sodium succinate in lyophilized form mixed with a buffering and/or alkalizing agents prior to lyophilization. Buffered lyophilized methylprednisolone sodium succinate may be prepared, for example, from methylprednisolone sodium succinate or from methylprednisolone hemi succinate with the aid of sodium hydroxide or sodium carbonate.

Buffering and/or alkalizing agents include but are not limited to ammonia solution, sodium citrate, potassium citrate, sodium acetate, sodium lactate, sodium dihydrogen phosphate dihydrate and disodium hydrogen phosphate, calcium phosphate, carbonated calcium phosphate, sodium carbonate, calcium carbonate, sodium bicarbonate, ammonium carbonate, diethanolamine, monoethanolamine, trolamine, magnesium hydroxide, sodium hydroxide, potassium hydroxide, or mixtures thereof.

Freeze-drying, technically known as lyophilization or cryodesiccation, is a dehydration process typically used to preserve a perishable material. Freeze-drying works by freezing the material and then reducing the surrounding pressure to allow the frozen water in the material to sublime directly from the solid phase to the gas phase.

The term "non-caking" used herein means that the powder does not cake or clump during manufacture, i.e., when mixed with excipients. Nor does it cake or dump upon storage, even under relatively humid conditions, e.g., a relative humidity of about 75% or greater and when stored for relatively long periods such as about 3 months or longer and even at elevated temperatures of about 40° C. or greater, or at any combination of such humidity, time and temperature parameters. Thus, the powder in accordance with the present invention will remain free flowing and non-caking during typical storage and use conditions.

The flow rate of the powder is tested according to USP (Chapter 1174). 100 g of powder is poured into an orifice and the time needed for the entire sample to flow out of the orifice is measured using a chronometer.

The Hausner ratio of the powder is calculated from the ratio of tapped density to bulk density according to the European Pharmacopoeia (Ph. Eur.) (Section 2.9.36).

The angle of repose of the powder is tested according to Ph. Eur. (Section 2.9.36) using standard apparatuses.

As used throughout the present description and claims, the terms "water-soluble" or "water-soluble excipient" refer to excipients, which in accordance with the corresponding definition of the United States Pharmacopeia, are characterized at least as soluble, namely, very soluble, freely soluble or soluble, and therefore a quantity of water less than 30 parts for each part of the ingredients is required for their dissolution.

As used throughout the present description and claims, the term "total impurities" refers to the sum of all methylprednisolone sodium succinate impurities, except for prednisolone and methylprednisolone 17 succinate.

As used throughout the present description and claims, the terms «%», «% weight/weight (w/w)» when referring to the active ingredient or inactive ingredients (excipients), mean the milligrams of active or inactive ingredient per 100 mg of the composition.

It is known in the prior art that methylprednisolone sodium succinate has a particularly bitter taste while at the same time is a very unstable substance, especially in the presence of moisture. Furthermore, methylprednisolone sodium succinate has poor flow.

Disclosed herein is the unexpected finding that mixtures of lyophilized methylprednisolone sodium succinate with pharmaceutically acceptable excipients, provide methylprednisolone sodium succinate compositions in the form of powder with optimum manufacturing characteristics and physicochemical stability.

The term "mixture" refers to compositions in which lyophilized methylprednisolone sodium succinate is dry mixed with one or more pharmaceutically acceptable excipients. Therefore, a "mixture" according to the present invention does not include a composition in which the excipients (except for possibly buffering and/or alkalizing excipients) are combined with methylprednisolone sodium succinate prior to lyophilization.

Importantly, it has been found that many processing difficulties such as poor flow, and tendency to absorb moisture and formation of cakes, which are prominent when methylprednisolone sodium succinate is not prepared by lyophilization are overcome by dry mixing lyophilized methylprednisolone sodium succinate with pharmaceutically acceptable excipients.

More specifically, the pharmaceutical composition in the form of powder for oral solution according to the invention comprises a mixture of lyophilized methylprednisolone sodium succinate and at least one or more water-soluble excipients.

The pharmaceutical compositions in the form of powder for oral solution according to the invention comprise one or more water-soluble pharmaceutically acceptable excipients. Any water-soluble pharmaceutically acceptable excipient known in the art as useful in powder compositions may be included, such as one or more members selected from the group consisting of diluents (fillers), sweeteners, lubricants, flavouring agents, buffering and/or alkalizing agents, antimicrobial agents, antioxidants, binders, glidants, and colourants. An excipient can serve multiple functions, for example, as both a filler and a sweetener.

A variety of materials may be used as diluents. Examples are spray-dried or anhydrous lactose, sucrose, dextrose, mannitol, sorbitol and others known in the art. The total concentration of diluent used in the powder compositions of the present invention is typically in the range of from 30% to 85%, more preferably in the range of from 55% to 80%, most preferably in the range of from 60% to 75%.

Sweeteners include, for example, sucrose, glucose, aspartame, mannitol, sodium saccharin, sucralose and any other pharmaceutically acceptable water-soluble sweetener or combination thereof. The total concentration of sweetener used in the powder compositions of the present invention is typically in the range of from 0.01% to 20%, more preferably in the range of from 0.05% to 10%, most preferably in the range of from 0.1% to 5%.

Examples of lubricants are boric acid, sodium oleate, sodium acetate, sodium lauryl sulfate, magnesium lauryl sulfate, sodium benzoate and the like. The total concentration of lubricant used in the powder compositions of the present invention is typically in the range of from 0.05% to 10%, more preferably in the range of from 0.5% to 8%, most preferably in the range of from 1% to 6%.

Appropriate flavouring agents include any of the many non-toxic natural or artificial flavouring agents known in the art. In particular, the flavouring agents used may include one or more of a variety of natural or artificial fruit flavours, including orange, lemon, lime, blueberry, cherry, apple, berry, pineapple, banana, grape, strawberry, watermelon, and kiwi flavouring, among others. Alternatively, or in addition, the flavouring agents may include one or more of natural or artificial vanilla, chocolate, peanut butter, pistachio, honey and caramel flavouring, among others. Solid forms, such as spray-dried forms of flavourants, are particularly useful in the powder compositions disclosed herein. The total concentration of flavouring agent may depend on a number of factors including the organoleptic effect desired. A flavouring agent is an optional ingredient in the powder compositions disclosed herein but, when used, will generally be present in a total concentration of from 0.05% to 5%.

Examples of binders are hydroxypropylcellulose, hydroxyethylcellulose, dextrose, xylitol, polyvinylpyrrolidone, sucrose, sorbitol, polyethylene glycol and the like. A binder is an optional ingredient in the powder compositions disclosed herein but, when used, will generally be present in a total concentration of from 0.05% to 0.5%.

Antimicrobial preservatives include but not limited to sodium benzoate, benzoic acid, boric acid, sorbic acid and their salts thereof, benzyl alcohol or mixtures thereof. An antimicrobial preservative is an optional ingredient in the powder compositions disclosed herein but, when used, will generally be present in a total concentration of from 0.05% to 0.15%.

Antioxidants which may be used in the present invention comprise, amongst others, butylated hydroxytoluene, butylated hydroxyanisole, ethylenediamine tetraacetic acid ("EDTA"), ascorbic acid, sodium metabisulfite and propyl gallate and any combination thereof. An antioxidant is an optional ingredient in the powder compositions disclosed herein but, when used, will generally be present in a total concentration of from 0.005% to 0.25%.

The dyes (colouring agents) include, for example, the yellow iron oxide, the red iron oxide and other colouring agents used in pharmaceutical technology. A dye is an optional ingredient in the powder compositions disclosed herein but, when used, will generally be present in a total concentration of from 0.005% to 0.15% w/w.

In a preferred embodiment, the pharmaceutical composition in the form of powder for oral solution according to the invention comprises one or more water-soluble pharmaceutical excipients selected from the group consisting of diluents, sweeteners and lubricants.

In a more preferred embodiment, the pharmaceutical composition in the form of powder for oral solution according to the invention comprises lyophilized methyprednisololone sodium succinate, and a diluent, which is mannitol, lactose or sorbitol, a sweetener, which is sucralose or sodium saccharin and a lubricant, which is sodium benzoate.

In a most preferred embodiment, the pharmaceutical composition in the form of powder for oral solution according to the invention comprises lyophilized methylprednisolone sodium succinate, and from 0% to 70% of a diluent, which is mannitol, lactose or sorbitol, form 0.2 to 4% of a sweetener, which is sucralose or sodium saccharin and from 1.5 to 5% of a lubricant, which is sodium benzoate.

Preferably, the lyophilized methylprednisolone sodium succinate in the compositions of the present invention is buffered, i.e. it is mixed with a buffering and/or alkalizing agents prior to lyophilization.

The pharmaceutical composition in the form of powder for oral solution of the present invention comprises preferably 5% to 40% methylprednisolone sodium succinate, more preferably comprises 10% to 35% methylprednisolone sodium succinate, most preferably comprises 20% to 30% methyprednisolone sodium succinate.

The excipients used in the powder composition of the present invention may be in different forms such as (amorphous or crystalline) powder, flakes, granules or pellets. It is preferred to use excipients which are not lyophilized, since they are easier to produce and in addition, they are cheaper and readily available from commercial sources.

It is also preferred to use excipients having certain particle size distributions. Preferably, the average particle size of the excipients used may range from 10 microns to 500 microns. Particle sizes of 10-250 microns are more preferred, particle sizes of 20-150 microns are even more preferred and particle sizes of 30-100 microns are most preferred. The term "micron" means "micrometre" By admixing lyophilized methylprednisolone sodium succinate with excipients having a narrow size distribution, the unit dosages exhibit reduced weight variation, as well as uniform content of the active ingredient. Such dosage units facilitate controlling the release rate and its consistency in the preparation of immediate release solutions.

Reduction of particle size of the excipients may be accomplished by using known techniques in the art, for example by sieving and/or milling.

It is also preferred to use excipients having certain moisture content. The moisture content is measured according to Ph. Eur. (Paragraph 2.2.32—loss on drying). A predetermined quantity of powder is placed in a pre-weighed weighing bottle. The powder is dried in an oven at 105 t 2° C. until a constant mass. Then the loss of the mass (% m/m) is calculated.

Preferably, the moisture content of the excipients used in the compositions should be less than 5%, more preferably less than 2.5%, and most preferably less than 1.0%.

Preferably, the moisture content of the powder for oral solution according to the invention should be less than 6%, more preferably less than 3%, and most preferably less than 1%.

The composition in the form of powder for oral solution of the invention overcomes the difficulties arising from the parenteral administration of prior art compositions comprising methylprednisolone sodium succinate. For instance, the oral dosage form according to the invention need not be administered by trained personnel and require less time, than commercial powders for injection, to be administered. Furthermore, compared to parenteral administration, which requires strict adherence to aseptic procedures, and some pain on injection is inevitable, the powder for oral solution according to the present invention provides enhanced accessibility to children and the elderly and increased patient compliance to medication.

The methylprednisolone sodium succinate powder for oral solution according to the present invention may be supplied, for example, in unit dosage bottles, or packets, or sachets, or vials that, upon dissolution, provide a unit dosage of methylprednisolone sodium succinate.

Dissolving the powder of the present invention requires addition of suitable solvent, which may be an aqueous medium, preferably water. For example, boiled then cooled tap water, distilled water, mineral water or tap water directly may be used.

The pharmaceutical composition in the form of methylprednisolone sodium succinate powder for oral solution according to the present invention may also be supplied in a vial with plunger and tear off cap. This dosage form of methylprednisolone sodium succinate comprises a dispensing cap and single-dose vial. The dispensing cap includes two caps, a reservoir cap which stores liquid (in some designs) or powder and tear-off cap. The single-dose vial contains a liquid, which is prepared specially to dissolve the content of the reservoir cap. This dosage form allows methylprednisolone sodium succinate to remain stable until the time of use. The dosage form, in this case, is used by removing the tear-off cap, then by pressing (pushing) the plunger into the vial shaking well then drinking the whole resulting solution or diluting it in another liquid. The plunger in this design has two roles, first as a reservoir cap to preserve methylprednisolone sodium succinate powder in it, second: a tool to push the powder into the vial through the tear off cap.

The powder for oral solution of the present invention preferably comprises, per dosage unit, from 26.5 mg of methylprednisolone sodium succinate, equivalent to 20 mg of methylprednisolone to 3978.0 mg of methylprednisolone sodium succinate, equivalent to 3000 mg of methylprednisolone.

The powder for oral solution of the present invention preferably comprises, per dosage unit, from 53.0 mg of methylprednisolone sodium succinate, equivalent to 40 mg of methylprednisolone to 2652.0 mg of methylprednisolone sodium succinate, equivalent to 2000 mg of methylprednisolone.

In another aspect, the present invention is directed to a process for the production of a non-caking, stable methylprednisolone sodium succinate powder composition comprising the steps of a) obtaining lyophilized methylprednisolone sodium succinate, b) obtaining one or more water-soluble pharmaceutically acceptable excipients, optionally, reducing their particle size by sieving and/or milling, c) dry mixing the lyophilized methylprednisolone sodium succinate of step a) and the one or more excipients of step b).

Preferably the loss on drying of the excipient(s) is measured just before the final mixing of the excipient(s) with the buffered lyophilized powder of methylprednisolone sodium succinate.

Preferably, the lyophilized methylprednisolone sodium succinate in step a) is buffered.

Optionally buffering/alkalizing agents may be also added during dry mixing in step c).

It will be appreciated by those skilled in the art that the present invention provides significant advances over techniques known in the art for preparing pharmaceutical powders suitable for oral solutions, since an alternative efficient, cost-effective and robust method for making non-caking, stable methylprednisolone sodium succinate powder compositions is provided. It will also be appreciated by those skilled in the art that the powder for oral solution of the present invention may be prepared using regular manufacturing equipment.

EXAMPLES

The following examples show the influence of the proposed, according to the invention, composition, on the flowability and physicochemical stability of methylprednisolone sodium succinate powder and palatability of the solution.

Example 1

Six powder compositions were manufactured based on powder mixtures.

The powder compositions were prepared as follows:

All excipients were sized and screened through a BSS #100 Sieve (150 microns). Lyophilized methylprednisolone sodium succinate (Trials I, II & III) or methylprednisolone sodium succinate granules (Trials I', II'& III') were blended in a suitable mixer with the excipients of Table 1. Loss on drying of all excipients used, were measured and found to be less than 0.5%.

The buffered lyophilized methylprednisolone sodium succinate was prepared as follows:

Methylprednisolone 21-hemisuccinate was suspended in 0.08M phosphate buffer, pH=7.5. Conversion to the sodium salt was carried out by slow addition of 10% sodium hydroxide until essentially all solids were dissolved. The final pH was 7.5 to 7.7. The solutions were sterile filtered and filled into 20 ml glass vials. Lyophilization was carried out by placing vials on the freeze drying shelf, freezing at −50° C. for 4-8 hrs. followed by primary drying at a shelf temperature of 10° C. and a chamber pressure of 100 microns Hg for 24 hours. Secondary drying was carried out for approximately 24 hrs at a shelf temperature of 30° C. and a chamber pressure of 100 microns Hg. Vials were stoppered under full vacuum.

TABLE 1

|  | Trial I & I' | Trial II & II' | Trial III & III' |
| --- | --- | --- | --- |
| Active ingredient |  | mg |  |
| Methylprednisolone Sodium Succinate* | 132.6 | 132.6 | 1326 |
| Excipients |  | mg |  |
| Lactose Monohydrate | — | 141.15 | 1411.5 |
| Sorbitol powder | 141.15 | — | — |
| Mannitol | 200 | 200 | 2000 |
| Sodium saccharine | 0.75 | 0.75 | 7.5 |
| Orange flavour | 0.5 | 0.5 | 5.0 |
| Sodium Benzoate | 25 | 25 | 250 |
| Total weight | 500 | 500 | 5000 |

*granules or buffered lyophilized powder

TABLE 2

|  | Flow rate (100 g/sec) | Hausner Ratio* | Angle of repose (degrees) | Loss on drying (%)** |
| --- | --- | --- | --- | --- |
| Trial I | 30 | 1.07 | 30 | 0.26 |
|  |  |  |  | 0.30 |
|  |  |  |  | 0.29 |

TABLE 2-continued

|  | Flow rate (100 g/sec) | Hausner Ratio* | Angle of repose (degrees) | Loss on drying (%)** |
| --- | --- | --- | --- | --- |
| Trial I' | 52 | 1.41 | 58 | 0.55 |
|  |  |  |  | 0.28 |
|  |  |  |  | 0.41 |
| Trial II | 34 | 1.17 | 28 | 0.22 |
|  |  |  |  | 0.25 |
|  |  |  |  | 0.28 |
| Trial II' | 59 | 1.43 | 55 | 0.55 |
|  |  |  |  | 0.44 |
|  |  |  |  | 0.31 |
| Trial III | 38 | 1.11 | 32 | 0.36 |
|  |  |  |  | 0.32 |
|  |  |  |  | 0.29 |
| Trial III' | 49 | 1.51 | 67 | 0.50 |
|  |  |  |  | 0.69 |
|  |  |  |  | 0.42 |

*Two measurements per sample were performed and the mean value calculated. The variation in the two measurements was less than 0.1%.

**Three measurements were performed in samples collected from different locations of the mixer.

Upon formulation of methylprednisolone sodium succinate granules with different excipients, the flow properties of the final powder mix were found to be insufficient for appropriate performance. By using buffered lyophilized methylprednisolone sodium succinate instead of methylprednisolone sodium succinate granules, the flow properties of the final powder were considerably improved. This is also depicted by the results of Table 2, since lower Hausner ratios of a material indicate better flow properties than higher ones. Additionally, angle of repose values of less than 35° is indicative for good or excellent flow properties. Instead, when the angle of repose exceed 50°, the flow is rarely acceptable for manufacturing process. Importantly, uniform loss on drying results were found only in case of lyophilized methylprednisolone sodium succinate

Example 2

Sixteen powder compositions were prepared as follows:

Buffered lyophilized methylprednisolone sodium succinate, prepared as explained in Example 1, was blended in a suitable mixer with the excipients of Table 3. The excipients had been sized and screened through a BSS #200 Sieve (75 microns) prior to mixture with the buffered lyophilized methylprednisolone sodium succinate. Loss on drying of all excipients used, were measured and found to be less than 0.5%.

A single palatability study making use of a three subject sensory panel was designed for the identification and optimization of the most effective taste masking agents. The organoleptic appeal of the solutions formed after dissolving the powders with tap water was assessed against the senses of taste and aftertaste. Each participant tasted the compositions and independently rated the palatability using a scale between 1 (least palatable) and 5 (most palatable).

TABLE 3

| Ingredient Trial No | A | B | C | D | E | F | G | H | Total weight |
|---|---|---|---|---|---|---|---|---|---|
| | | | | mg per sachet | | | | | |
| 1 | 132.6 | 150.0 | 50.00 | 141.6 | 25.00 | 0.8 | — | — | 500.0 |
| 2 | 132.6 | 150.0 | 50.00 | 141.9 | 25.00 | — | 0.50 | — | 500.0 |
| 3 | 132.6 | 150.0 | 50.00 | 141.1 | 25.00 | 0.8 | — | 0.50 | 500.0 |
| 4 | 132.6 | 150.0 | 50.00 | 141.4 | 25.00 | — | 0.50 | 0.50 | 500.0 |
| 5 | 132.6 | — | — | 341.6 | 25.00 | 0.8 | — | — | 500.0 |
| 6 | 132.6 | — | — | 341.9 | 25.00 | — | 0.50 | — | 500.0 |
| 7 | 132.6 | — | — | 341.1 | 25.00 | 0.8 | — | 0.50 | 500.0 |
| 8 | 132.6 | — | — | 341.4 | 25.00 | — | 0.50 | 0.50 | 500.0 |
| 9 | 1326 | — | — | 3542 | 125.0 | 7.00 | — | — | 5000 |
| 10 | 1326 | — | — | 3544 | 125.0 | — | 5.00 | — | 5000 |
| 11 | 1326 | — | — | 3537 | 125.0 | 7.00 | — | 5.00 | 5000 |
| 12 | 1326 | — | — | 3539 | 125.0 | — | 5.00 | 5.00 | 5000 |
| 13 | 1326 | — | — | 3539 | 125.0 | 10.0 | — | — | 5000 |
| 14 | 1326 | — | — | 3524 | 125.0 | 25.0 | — | — | 5000 |
| 15 | 1326 | — | — | 3524 | 125.0 | — | 10.0 | — | 5000 |
| 16 | 1326 | — | — | 3524 | 125.0 | — | 25.0 | — | 5000 |

A: Methylprednisolone sodium succinate; B: Lactose monohydrate; C: Sorbital powder; D: Mannitol; E: Sodium benzoate; F: Sodium saccharin; G: Sucralose; H: Vanillin As revealed from the results of Tables 4 & 5 below, mixtures of buffered lyophilized methylprednisolone sodium succinate with water-soluble excipients, can provide a methylprednisolone sodium succinate powder with optimum manufacturing characteristics. Additionally, upon proper selection of taste-masking excipients, they can provide oral solutions, after dissolving the powder with water, which exhibit exceptional taste and aftertaste. The total score of Table 4 is the sum of the values given by the three members of the sensory panel.

TABLE 4

| | Total score | |
|---|---|---|
| Trial ID | Taste | Aftertaste |
| Trial 1 | 16 | 15 |
| Trial 2 | 15 | 14 |
| Trial 3 | 18.5 | 17 |
| Trial 4 | 16.5 | 17 |
| Trial 5 | 16.5 | 15 |
| Trial 6 | 15 | 14 |
| Trial 7 | 17.5 | 16 |
| Trial 8 | 18.5 | 16 |
| Trial 9 | 9 | 7 |
| Trial 10 | 11 | 9 |
| Trial 11 | 14.5 | 10 |
| Trial 12 | 13.5 | 11 |
| Trial 13 | 15 | 12 |
| Trial 14 | 18.5 | 16 |
| Trial 15 | 18 | 20 |
| Trial 16 | 19.5 | 21.5 |

TABLE 5

| | Appearance | Hausner Ratio* | Loss on drying (%)** |
|---|---|---|---|
| Trial 1 | White to almost white powder | 1.07 | 0.25<br>0.29<br>0.29 |
| Trial 2 | White to almost white powder | 1.11 | 0.25<br>0.28<br>0.21 |
| Trial 3 | White to almost white powder | 1.05 | Not performed |
| Trial 4 | White to almost white powder | 1.07 | 0.22<br>0.28<br>0.27 |
| Trial 4 | White to almost white powder | 1.07 | 0.25<br>0.24<br>0.31 |
| Trial 6 | White to almost white powder | 1.04 | Not performed |
| Trial 7 | White to almost white powder | 1.11 | 0.36<br>0.32<br>0.29 |
| Trial 8 | White to almost white powder | 1.14 | 0.30<br>0.39<br>0.32 |
| Trial 9 | White to almost white powder | 1.08 | 0.32<br>0.39<br>0.42 |
| Trial 10 | White to almost white powder | 1.12 | 0.20<br>0.29<br>0.22 |
| Trial 11 | White to almost white powder | 1.16 | Not performed |
| Trial 12 | White to almost white powder | 1.01 | 0.31<br>0.32<br>0.35 |
| Trial 13 | White to almost white powder | 1.04 | Not performed |
| Trial 14 | White to almost white powder | 1.06 | Not performed |
| Trial 15 | White to almost white powder | 1.13 | 0.31<br>0.39<br>0.34 |
| Trial 16 | White to almost white powder | 1.04 | 0.30<br>0.29<br>0.22 |

*Two measurements per sample were performed and the mean value calculated. The variation in the two measurements was less than 0.1%.
**Three measurements were performed in samples collected from different locations of the mixer.

Example 3

Powder compostions of Trials 15 & 16 of Example 2 where formulated by using non-lyophilized methylprednisolone sodium succinate granules (Trials 15 & 16) instead of lyophilized methylprednisolone sodium succinate.

The compositions were studied in relation to their stability at storage conditions of 40° C. temperature and 75% relative humidity for one and three months. The quantitative determination of assay and methylprednisolone sodium succinate and its impurities in the prepared compositions, before and after the storage period, was carried out by HPLC.

TABLE 6

| Trial | #15 | #15' | #15 | #15' | #15 | #15' |
|---|---|---|---|---|---|---|
| | Initial | | T = 1 month | | T = 3 months | |
| Appearance | White to almost white powder | White to almost white powder | White to almost white powder | White to almost white powder, caked | White to almost white powder | Almost white powder, caked |
| Loss on drying | 0.33% | 0.49% | 0.41% | 0.96% | 0.65% | 2.1% |
| Assay | 98.9% | 98.6% | 98.3% | 97.9% | 97.6% | 97.1% |
| Free Methylprednisolone | 0.4% | 0.5% | 0.7% | 1.0% | 0.9% | 1.6% |
| Methylprednisolone 17 succinate | 0.7% | 0.6% | 0.7% | 0.6% | 0.7% | 0.6% |
| Any other impurity | 0.06% | 0.07% | 0.08% | 0.1% | 0.08% | 0.2% |
| Total impurity | 0.1% | 0.1% | 0.1% | 0.2% | 0.1% | 0.4% |

TABLE 7

| Trial | #16 | #16' | #16 | #16' | #16 | #16' |
|---|---|---|---|---|---|---|
| | Initial | | T = 1 month | | T = 3 months | |
| Appearance | White to almost white powder | White to almost white powder | White to almost white powder | White to almost white powder, caked | White to almost white powder | Almost white powder, caked |
| Loss on drying | 0.21% | 0.46% | 0.31% | 0.82% | 0.45% | 1.9% |
| Assay | 98.9% | 98.6% | 98.0% | 97.6% | 97.7% | 97.0% |
| Free Methyl-prednisolone | 0.3% | 0.4% | 0.6% | 1.0% | 0.8% | 1.5% |
| Methyl-prednisolone 17 succinate | 0.5% | 0.6% | 0.7% | 0.7% | 0.7% | 0.7% |
| Any other impurity | 0.05% | 0.07% | 0.06% | 0.1% | 0.06% | 0.2% |
| Total impurities | 0.1% | 0.1% | 0.1% | 0.2% | 0.1% | 0.4% |

Interestingly, as revealed from the results of Tables 6 & 7 only mixtures of lyophilized methylprednisolone sodium succinate with water-soluble excipients can provide a methylprednisolone sodium succinate powder with optimum physicochemical stability without formation of cakes due to high environmental humidity.

The invention claimed is:

1. Pharmaceutical composition in the form of powder for reconstitution for oral administration comprising a mixture of buffered lyophilized methylprednisolone sodium succinate and one or more water-soluble pharmaceutically acceptable excipients, wherein the one or more water-soluble pharmaceutically acceptable excipients are not lyophilized and are selected from the group consisting of from 60% to 75% (w/w), diluent, from 0.1 to 0.5% (w/w), sweetener and from 1 to 6% of (w/w) a lubricant.

2. Pharmaceutical composition according to claim 1, wherein the diluent is mannitol or lactose or sorbitol, the sweetener is sucralose or sodium saccharin and the lubricant is sodium benzoate.

3. Pharmaceutical composition according to claim 1, wherein the total concentration of the diluent, which is mannitol, lactose or sorbitol is from 60% to 70% (w/w), the total concentration of the sweetener which is sucralose or sodium saccharin is from 0.2% to 4% (w/w) and the total concentration of the lubricant which is sodium benzoate is from 1.5% to 5% (w/w).

4. Pharmaceutical composition according claim 1, wherein the concentration of methylprednisolone sodium succinate is from 20% to 30% (w/w).

5. Pharmaceutical composition according to claim 1, wherein the average particle size of the one or more water-soluble pharmaceutically acceptable excipients is from 30 to 100 microns.

* * * * *